(12) United States Patent
Li et al.

(10) Patent No.: US 10,640,474 B2
(45) Date of Patent: May 5, 2020

(54) HYBRID SCORCH RETARDANT/CURE CO-AGENT

(71) Applicant: Dow Global Technologies LLC, Midland, MI (US)

(72) Inventors: Wei Li, Shanghai (CN); Yabin Sun, Shanghai (CN); Jeffrey M. Cogen, Collegeville, PA (US); Yu Cai, Shanghai (CN)

(73) Assignee: Dow Global Technologies LLC, Midland, MI (US)

( * ) Notice: Subject to any disclaimer, the term of this patent is extended or adjusted under 35 U.S.C. 154(b) by 43 days.

(21) Appl. No.: 15/578,325

(22) PCT Filed: Jun. 16, 2015

(86) PCT No.: PCT/CN2015/081532
§ 371 (c)(1),
(2) Date: Nov. 30, 2017

(87) PCT Pub. No.: WO2016/201616
PCT Pub. Date: Dec. 22, 2016

(65) Prior Publication Data
US 2018/0148421 A1 May 31, 2018

(51) Int. Cl.
| | | |
|---|---|---|
| *C07D 251/30* | (2006.01) | |
| *C07D 251/34* | (2006.01) | |
| *C08F 255/02* | (2006.01) | |
| *C08K 5/14* | (2006.01) | |
| *C08K 5/3492* | (2006.01) | |
| *H01B 3/44* | (2006.01) | |

(52) U.S. Cl.
CPC ......... *C07D 251/34* (2013.01); *C07D 251/30* (2013.01); *C08F 255/02* (2013.01); *C08K 5/14* (2013.01); *C08K 5/34924* (2013.01); *H01B 3/441* (2013.01)

(58) Field of Classification Search
CPC ...... C07D 251/34; C07D 251/30; C08K 5/14; C08K 5/34924; H01B 3/441; C08F 255/02
See application file for complete search history.

(56) References Cited

U.S. PATENT DOCUMENTS

| | | | | |
|---|---|---|---|---|
| 3,736,173 A | * | 5/1973 | Okada et al. | ........... B29B 7/005 |
| | | | | 427/222 |
| 4,018,852 A | | 4/1977 | Schober | |
| 4,256,558 A | * | 3/1981 | Inata | ..................... C08F 283/02 |
| | | | | 264/477 |
| 4,857,600 A | | 8/1989 | Gross et al. | |
| 5,246,783 A | | 9/1993 | Spenadel | |
| 5,272,236 A | | 12/1993 | Lai et al. | |
| 5,278,272 A | | 1/1994 | Lai et al. | |
| 5,346,961 A | | 9/1994 | Shaw et al. | |
| 5,575,965 A | | 11/1996 | Caronia et al. | |
| 5,986,028 A | | 11/1999 | Lai et al. | |
| 6,496,629 B2 | | 12/2002 | Ma | |
| 6,714,707 B2 | | 3/2004 | Rossi | |
| 7,355,089 B2 | | 4/2008 | Chang et al. | |
| 7,504,347 B2 | | 3/2009 | Poon et al. | |
| 7,514,517 B2 | | 4/2009 | Hoenig et al. | |
| 7,524,911 B2 | | 4/2009 | Karjala et al. | |
| 7,579,408 B2 | | 8/2009 | Walton et al. | |
| 7,582,716 B2 | | 9/2009 | Liang et al. | |
| 2002/0169238 A1 | * | 11/2002 | Caronia | ................... C08K 5/14 |
| | | | | 524/100 |
| 2013/0149645 A1 | | 6/2013 | Takemura et al. | |
| 2015/0203701 A1 | | 7/2015 | Sun et al. | |

FOREIGN PATENT DOCUMENTS

| | | |
|---|---|---|
| CN | 102911619 A | 2/2013 |
| CN | 104629159 A | 5/2015 |
| JP | 4523801 B2 | 8/2010 |
| JP | 2015013846 A | 1/2015 |
| WO | 2015/078877 A1 | 6/2015 |

OTHER PUBLICATIONS

Machine English translation of JP 4523801 Yukio, Aug. 11, 2010.*

* cited by examiner

*Primary Examiner* — Patrick D Niland
(74) *Attorney, Agent, or Firm* — Quarles & Brady LLP

(57) ABSTRACT

A family of novel hybrid compounds comprise a hindered phenolic scorch retardant and an allyl isocyanurate cure co-agent. Combining these two functionalities into a single molecule provides a synergy between the allyl isocyanurate and phenolic groups that achieves an improved balance between curing and scorch.

4 Claims, 1 Drawing Sheet

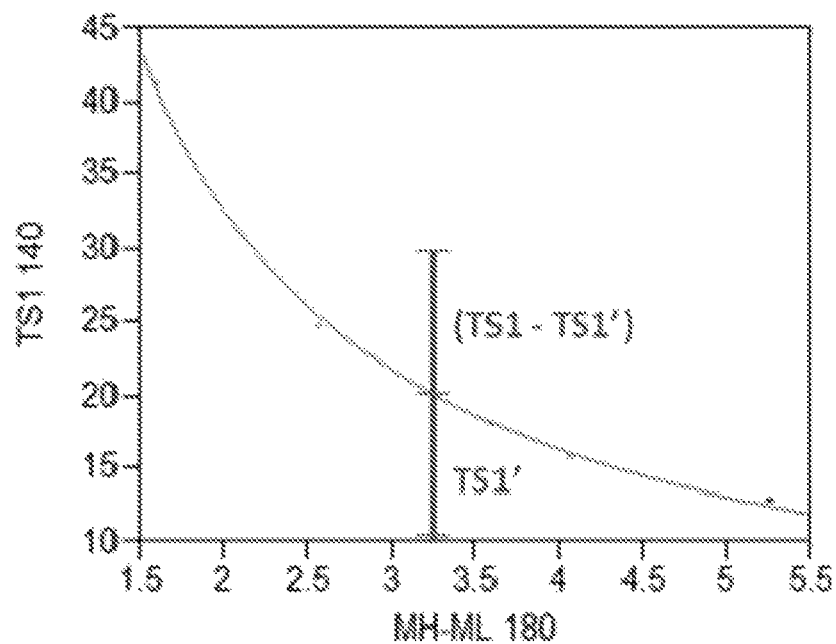

HYBRID SCORCH RETARDANT/CURE CO-AGENT

FIELD OF THE INVENTION

This invention relates to the extrusion of polymeric compositions, particularly ethylene-based polymers for use as sheathing for electrical cables. In one aspect the invention relates to the promotion of the cure of the ethylene-based polymer while in another aspect, the invention relates to the prevention of scorch of the ethylene-based polymer during the extrusion process.

BACKGROUND OF THE INVENTION

Peroxide-initiated crosslinking is practiced widely to improve the mechanical and thermal properties of ethylene-rich polyolefins for power transmission cable applications. Although fast and adequate crosslinking is desired at the vulcanization stage, premature crosslinking (scorch) needs to be avoided as much as possible because it adversely affects the quality of the products. Furthermore, scorch causes gelation and adhesion of polymer gel to the internal surfaces of the extruder, which can result in extruder plugging and this, in turn, in extruder downtime to remove the plugs.

To retard scorch the industry relies extensively on phenolic antioxidants. However, the industry also relies extensively on triallyl isocyanurate as a crosslinking co-agent to improve curing efficiency. This combination of scorch retardant and cure co-agent, while effective at one level, proves to be a difficult balance to achieve and maintain, and leaves space for operational improvement.

JP 4 523 801 B2 discloses an isocyanuric acid compound (Formula 1, an isocyanuric acid/phenol compound) that is used as an antioxidant in polymeric materials.

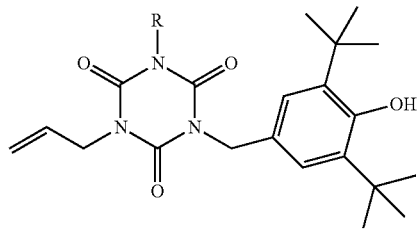

(Formula 1)

R represents an allyl group or a 3,5-di-tert-butyl-4-hydroxybenzyl group. This reference teaches the synthesis of the compound and its possible use in polymeric materials to improve the compatibility of the antioxidant with the host polymer and to retard its exudation from the polymer. The reference does not teach the use of this compound in polymeric materials to improve the scorch performance by the synergistic effect of the hindered phenol and the allyl isocyanurate groups. The reference also teaches only a very general composition of polymeric material and an isocyanuric acid/phenol compound. It does not teach a composition of a polymeric material, a peroxide, and an allyl isocyanuric acid/phenol compound.

US 2013/0149645 A1 discloses a chemically amplified negative resist composition used in the field of semiconductor fabrication. The composition comprise an isocyanuric acid with a general structure depicted as Formula 2.

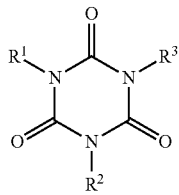

(Formula 2)

$R^1$, $R^2$ and $R^3$ may be the same or different, at least one of $R^1$, $R^2$ and $R^3$ is a crosslinking group or a monovalent organic group having a reaction site susceptible to crosslinking, and the remaining R groups are a monovalent hydrocarbon group of 1-20 carbon atoms. This general structure is very broad and may include an isocyanuric acid/phenol structure. However, it does not teach this structure in the context of a hybrid scorch retardant/cure co-agent for use in the extrusion of ethylene-based polymers.

SUMMARY OF THE INVENTION

In one embodiment the invention is a family of novel hybrid compounds which comprise a hindered phenolic scorch retardant and an allyl isocyanurate cure co-agent. Combining these two functionalities into a single molecule provides a synergy between the allyl isocyanurate and phenolic groups that achieves an improved balance between curing and scorch.

In one embodiment the invention is a compound of Formula 3, 4, 5 or 6:

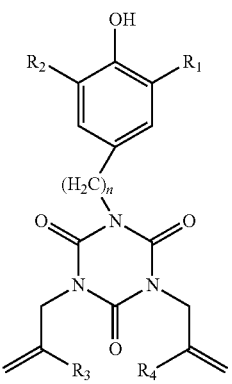

(Formula 3)

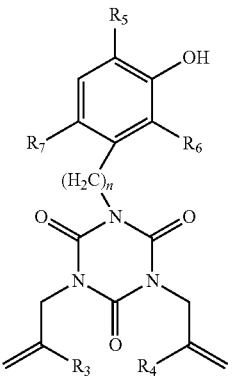

(Formula 4)

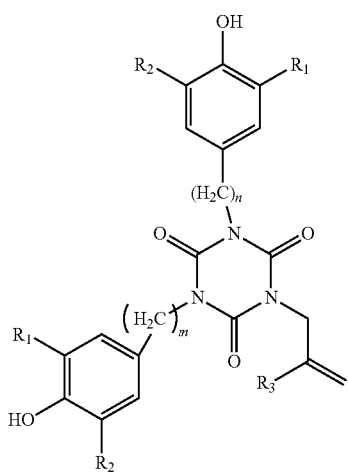

(Formula 5)

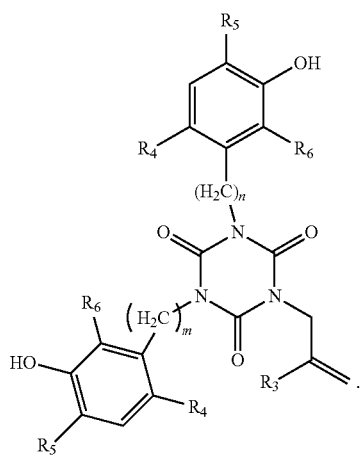

(Formula 6)

In Formulae 3 and 4, each of $R_1$, $R_2$, $R_5$, $R_6$, and $R_7$ represent independently hydrogen or an alkyl group of 1 to 10 carbon atoms, especially H, $CH_3$ or tert-butyl; each of $R_3$ and $R_4$ represent independently H or $CH_3$; and n is from 0 to 20. In Formulae 5 and 6, each of $R_1$, $R_2$, $R_4$, $R_5$ and $R_6$ represent independently hydrogen or an alkyl group of 1 to 10 carbon atoms, especially H, $CH_3$ or tert-butyl; each of $R_3$ and $R_4$ represent independently H or $CH_3$; and each of m and n is independently from 0 to 20.

In one embodiment the invention is a composition comprising:

(A) An ethylene-based polymer, (B) A peroxide, and (B) At least one compound of Formula 3, 4, 5 or 6.

In one embodiment the invention is a crosslinked article made from a composition comprising an ethylene-based polymer, a peroxide and at least one compound of Formula 3, 4, 5 or 6. In one embodiment the article is a wire or cable sheath.

BRIEF DESCRIPTION OF THE DRAWINGS

The FIG. 1 is plot or curve showing the relationship between TS1 at 140° C. and (MH-ML) at 180° C.

DETAILED DESCRIPTION OF THE PREFERRED EMBODIMENT

Definitions

Unless stated to the contrary, implicit from the context, or customary in the art, all parts and percents are based on weight and all test methods are current as of the filing date of this disclosure. For purposes of United States patent practice, the contents of any referenced patent, patent application or publication are incorporated by reference in their entirety (or its equivalent US version is so incorporated by reference) especially with respect to the disclosure of synthetic techniques, product and processing designs, polymers, catalysts, definitions (to the extent not inconsistent with any definitions specifically provided in this disclosure), and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, weight percentages, etc., is from 100 to 1,000, then the intent is that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 0.9, 1.1, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the amounts of various components in the inventive composition, and the various characteristics and properties by which these compositions and the wire and cable sheathing made from these compositions are defined.

"Wire" and like terms mean a single strand of conductive metal, e.g., copper or aluminum, or a single strand of optical fiber.

"Cable", "power cable" and like terms mean at least one wire or optical fiber within a sheath, e.g., an insulation covering or a protective outer jacket. Typically, a cable is two or more wires or optical fibers bound together, typically in a common insulation covering and/or protective jacket. The individual wires or fibers inside the sheath may be bare, covered or insulated. Combination cables may contain both electrical wires and optical fibers. The cable, etc. can be designed for low, medium and high voltage applications. Typical cable designs are illustrated in U.S. Pat. Nos. 5,246,783; 6,496,629 and 6,714,707.

"Composition" and like terms mean a mixture or blend of two or more components.

"Polymer" and like terms means a macromolecular compound prepared by reacting (i.e., polymerizing) monomers of the same or different type. "Polymer" includes homopolymers and interpolymers.

"Interpolymer" means a polymer prepared by the polymerization of at least two different monomers. This generic term includes copolymers, usually employed to refer to polymers prepared from two different monomers, and polymers prepared from more than two different monomers, e.g., terpolymers, tetrapolymers, etc. "Interpolymer" includes all forms of interpolymers, e.g., random, block, etc.

"Ethylene-based polymer", "ethylene polymer", "ethylene-based interpolymer" and like terms refer to a polymer that comprises a majority amount of polymerized ethylene based on the weight of the polymer and, optionally, may comprise at least one comonomer.

Ethylene-Based Polymer

The ethylenic polymers used in the practice of this invention include both homopolymers and interpolymers, random and blocky copolymers, and functionalized (e.g., ethylene vinyl acetate, ethylene ethyl acrylate, etc.) and non-functionalized polymers. The ethylenic interpolymers include elastomers, flexomers and plastomers. The ethylene polymer comprises at least 50, preferably at least 60 and more preferably at least 80, weight percent (wt %) of units derived from ethylene. If an ethylenic interpolymer, then the other units of the ethylenic interpolymer are typically derived from one or more alpha-olefins.

The alpha-olefin is preferably a $C_{3-20}$ linear, branched or cyclic alpha-olefin. Examples of $C_{3-20}$ alpha-olefins include propene, 1-butene, 4-methyl-1-pentene, 1-hexene, 1-octene, 1-decease, 1-dodecene, 1-tetradecene, 1-hexadecene, and 1-octadecene. The alpha-olefins also can contain a cyclic structure such as cyclohexane or cyclopentane, resulting in an alpha-olefin such as 3-cyclohexyl-1-propene (allyl cyclohexane) and vinyl cyclohexane. Although not alpha-olefins in the classical sense of the term, for purposes of this invention certain cyclic olefins, such as norbornene and related olefins, particularly 5-ethylidene-2-norbornene, are alpha-olefins and can be used in place of some or all of the alpha-olefins described above. Similarly, styrene and its related olefins (for example, alpha-methylstyrene, etc.) are alpha-olefins for purposes of this invention. Illustrative ethylenic interpolymers include copolymers of ethylene/propylene, ethylene/butene, ethylene/1-hexene, ethylene/1-octene, ethylene/styrene, and the like. Illustrative ethylenic terpolymers include ethylene/propylene/1-octene, ethylene/propylene-/butene, ethylene/butene/1-octene, ethylene/propylene/diene monomer (EPDM) and ethylene/butene/styrene.

Examples of ethylenic polymers useful in the practice of this invention include high density polyethylene (HDPE); medium density polyethylene (MDPE); low density polyethylene (LDPE); very low density polyethylene (VLDPE); homogeneously branched, linear ethylene/alpha-olefin copolymers (e.g. TAFMER™ by Mitsui Petrochemicals Company Limited and EXACT™ by DEX-Plastomers); homogeneously branched, substantially linear ethylene/alpha-olefin polymers (e.g., AFFINITY™ polyolefin plastomers and ENGAGE™ polyolefin elastomers available from The Dow Chemical Company); and ethylene block copolymers (INFUSE™ also available from The Dow Chemical Company). The substantially linear ethylene copolymers are more fully described in U.S. Pat. Nos. 5,272,236; 5,278,272 and 5,986,028, and the ethylene block copolymers are more fully described in U.S. Pat. Nos. 7,579,408; 7,355,089; 7,524,911; 7,514,517; 7,582,716 and 7,504,347.

Olefinic interpolymers of particular interest for use in the practice of this invention are LDPE, linear low density polyethylene (LLDPE) and HDPE. These ethylenic copolymers are commercially available from a number of different sources including The Dow Chemical Company under such trademarks as DOWLEX™, ATTANE™ and FLEXOMER™.

One preferred polymer is a high pressure low density polyethylene (LDPE). One conventional high pressure process is described in Introduction to Polymer Chemistry, Stille, Wiley and Sons, New York, 1962, pages 149 to 151. The high pressure processes are typically free radical initiated polymerizations conducted in a tubular reactor or a stirred autoclave. In the stirred autoclave, the pressure is in the range of 10,000 to 30,000 pounds per square inch (psi) (70 to 210 kilopascals (kPa)) and the temperature is in the range of 175 to 250° C., and in the tubular reactor, the pressure is in the range of 25,000 to 45,000 psi (170 to 310 kPa) and the temperature is in the range of 200 to 350° C.

The amount of ethylene polymer present in the compositions of this invention can vary widely, but the amount is typically of 50 to 99.9, more typically 70-99.5 and even more typically 80-99.5, wt % based on the total weight of the composition. The ethylene polymer can be present as a single polymer, e.g., LDPE, or as a blend of two or more polymers, e.g., LDPE and MDPE.

Cure Package

The cure package comprises a peroxide initiator and, optionally, a coagent. Examples of the peroxide initiator include dicumyl peroxide; bis(alpha-t-butyl-peroxyisopropyl)benzene; isopropylcumyl t-butyl peroxide; t-butylcumylperoxide; di-t-butyl peroxide; 2,5-bis(t-butylperoxy)-2,5-dimethylhexane; 2,5-bis(t-butylperoxy)-2,5-dimethylhexyne-3; 1,1-bis(t-butylperoxy)3,3,5-trimethylcyclohexane; isopropylcumyl cumylperoxide; di(isopropylcumyl) peroxide; and mixtures of two or more such initiators. Peroxide curing agents are used typically in amounts of 0.01 to 10, more typically 0.1 to 5, wt % based on the weight of the composition.

Various curing coagents (as well as boosters or retarders) can be used in combination with the peroxide initiator, and these include triallyl isocyanurate; ethoxylated bisphenol A dimethacrylate; alpha-methyl styrene dimer (AMSD); and the other co-agents described in U.S. Pat. Nos. 5,346,961 and 4,018,852. Coagents are used, if used at all, typically in amounts of greater than 0 (e.g., 0.01) to 3, more typically 0.1 to 0.5 and even more typically 0.2 to 0.4, wt % based on the weight of the composition. However, while individual curing coagents and/or cure retardants can be used in the practice of this invention, these are generally disfavored as unnecessary given the use of the hybrid scorch retardant/cure coagents described above.

Hybrid Scorch Retardant/Cure Coagent

The hybrid scorch retardant/cure coagent used in the practice of this invention are described above. They can be used alone, in combination with one another, and/or in combination with one or more cure coagents and/or scorch retardants. In one embodiment the hybrid scorch retardant/cure coagent is used in the absence of a non-hybrid cure coagent or scorch retardant. In one embodiment the hybrid scorch retardant/cure coagent is used in combination with one or more of a non-hybrid cure coagent or scorch retardant.

The hybrid scorch retardant/cure coagent is used typically in an amount of 0.01 to 10 wt %, more typically in an amount of 0.1 to 5 wt %, based on the weight of the composition.

Additive and Fillers

The compositions of this invention may contain additives including but not limited to processing aids, coupling agents, ultraviolet absorbers or stabilizers, antistatic agents, nucleating agents, slip agents, plasticizers, lubricants, viscosity control agents, tackifiers, anti-blocking agents, surfactants, extender oils, acid scavengers, and metal deactivators. Additives, other than fillers, are typically used in amounts ranging from 0.01 or less to 10 or more wt % based on the weight of the composition. Fillers are generally added in larger amounts although they the amount can range from as low as 0.01 or less to 50 or more wt % based on the weight of the composition. Examples of fillers include but are not limited to clays, precipitated silica and silicates, fumed silica, calcium carbonate, ground minerals, and carbon blacks with typical arithmetic mean particle sizes larger than 15 nanometers.

Compounding and Fabrication

Compounding of a cable insulation material can be effected by standard equipment known to those skilled in the art. Examples of compounding equipment are internal batch mixers, such as a BANBURY™ or BOLLING™ internal mixer. Alternatively, continuous single, or twin screw, mixers can be used, such as FARREL™ continuous mixer, a WERNER AND PFLEIDERER™ twin screw mixer, or a BUSS™ kneading continuous extruder.

A cable containing an insulation layer comprising a composition of the invention can be prepared with various types of extruders, e.g., single or twin screw types. A description of a conventional extruder can be found in U.S. Pat. No. 4,857,600. An example of co-extrusion and an extruder can be found in U.S. Pat. No. 5,575,965. A typical extruder has a hopper at its upstream end and a die at its downstream end. The hopper feeds into a barrel, which contains a screw. At the downstream end, between the end of the screw and the die, there is a screen pack and a breaker plate. The screw portion of the extruder is considered to be divided up into three sections, the feed section, the compression section, and the metering section, and two zones, the back heat zone and the front heat zone, the sections and zones running from upstream to downstream. In the alternative, there can be multiple heating zones (more than two) along the axis running from upstream to downstream. If it has more than one barrel, the barrels are connected in series. The length to diameter ratio of each barrel is in the range of about 15:1 to about 30:1. In wire coating where the polymeric insulation is crosslinked after extrusion, the cable often passes immediately into a heated vulcanization zone downstream of the extrusion die. The heated cure zone can be maintained at a temperature in the range of about 200 to about 350° C., preferably in the range of about 170 to about 250° C. The heated zone can be heated by pressurized steam, or inductively heated pressurized nitrogen gas.

The invention is illustrated by the following examples.

EXAMPLES

Materials

DXM-446 is low density polyethylene pellets from the Dow Chemical Company. Dicumyl peroxide (DCP, CAS No: 80-43-3) was purchased from Shanghai Fang Rui Da chemical company. IRGANOX™ 1076 (CAS No: 2082-79-3) and IRGANOX™ PS-802 was provided by Ciba Specialty Chemicals. CYANOX™ 1790 was provided by Cytec company. Diallyl Isocyanurate (DAIC, CAS No: 6294-79-7) was purchase from TCI. 2-Ethylhexyl bromide (CAS No: 18908-66-2) was purchased from Maya Reagents. 2-tert-Butyl-6-methylphenol; 2,6-Di-tert-butylphenol; hexamethylphosphoric triamide (HMTA) and paraformaldehyde were purchased from Aldrich. All materials were used as received without further purification.

Synthesis of 1,3-Diallyl-5-(2-ethylhexyl)-1,3,5-triazinane-2,4,6-trione (DAIC-EH)

Diallyl isocyanurate (2 g, 0.0096 mol) and 2-Ethylhexyl bromide (1.85 g, 0.0096 mol) are dissolved in dimethylformamide (DMF) (20 mL), and potassium carbonate (1.33 g, 0.0096 mol) is suspended in this solution. The mixture is stirred and heated to 120° C. Stirring continues at 120° C. for 4 hours, the mixture is cooled to room temperature and DMF is removed by rotary evaporation. The residue is re-dissolved in ethyl acetate. This solution is washed by water, 5 wt % hydrochloric acid (HCl, 10 mL), and brine. The organic solution is dried over magnesium sulfate, filtered and taken to dryness by rotary evaporation and dynamic vacuum. Clear oil (yield: 85%). 1H NMR (400 MHz, CDCl3) δ 5.87 (m, 2H), 5.25 (m, 4H), 4.49 (d, 4H), 3.81 (t, 2H), 1.81 (m, 1H), 1.27 (m, 8H), 0.87 (m, 6H). ESI-MS (m/z, MH+) Calculated: 322.42 Da; Found: 322.20 Da.

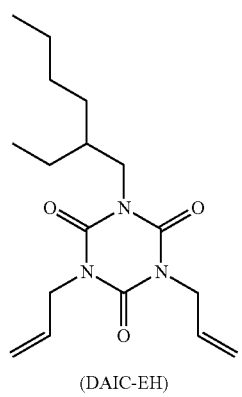 [SMILES: C=CCn1c(=O)n(CC=C)c(=O)n(CC(CC)CCCC)c1=O]

(DAIC-EH)

Synthesis of Inventive Compounds

Synthesis of IC-1

To a solution of 2,6-di-tert-butylphenol (2.06 g, 0.01 mol) in DMF is added paraformaldehyde (0.45 g, 0.015 mol), diallyl isocyanurate (3.14 g, 0.015 mol) and HMTA (0.18 g, 0.001 mol). The resulting solution is stirred at 120° C. for 8 hours. The reaction mixture is then quenched by addition of water and extracted with ethyl acetate. The combined organic layers are washed with brine, dried over sodium sulfate (Na2SO4), and concentrated under reduced pressure. The crude material is purified by flash column chromatography to obtain the desired product. 1H NMR (400 MHz, CDCl3) δ 7.36 (s, 2H), 5.86 (m, 2H), 5.30 (m, 2H), 5.23 (m, 2H), 4.97 (s, 2H), 4.47 (d, 4H), 1.43 (s, 18H).

Synthesis of IC-2

Synthesis of IC-2 is the same as that for IC-1 except that the phenol used is 2-tert-butyl-6-methylphenol. 1H NMR (400 MHz, CDCl3) δ 7.30 (d, 1H), 7.12 (d, 1H), 5.85 (m, 2H), 5.27 (q, 4H), 4.94 (s, 2H), 4.79 (d, 1H), 4.47 (m, 4H), 2.22 (s, 3H), 1.38 (s, 9H). HRMS (m/z) Calculated: for C21H27N3NaO4+[M+Na+]: 408.1894; found 408.1880.

Synthesis of IC-3 and IC-4

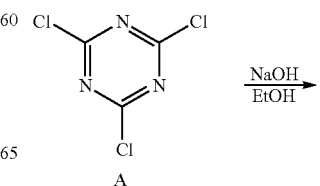

A

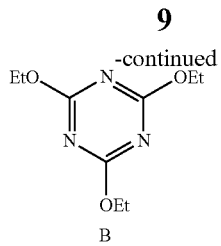

B

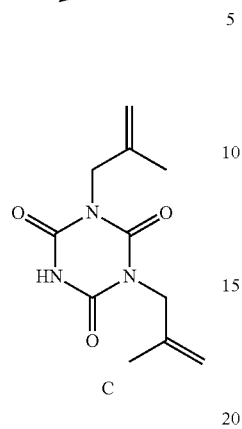

C

Synthesis of B 12.5 g (300 mmol) of sodium hydroxide and 100 ml of ethanol are added to a 500-ml four-necked flask. 18.4 g (100 mmol) of cyanuric chloride is added over 30 min and the mixture is cooled and agitated with the protection of an ice bath. After the completion of cyanuric chloride addition, the ice bath is removed and the mixture is continuously agitated at room temperature (about 23° C.) for 1.5 hours. The precipitate is removed from the reaction solution by filtration. After ethanol is removed from the filtrate by distillation under reduced pressure, crude product B is obtained and is used without further purification.

Synthesis of C 30 ml dimethyl sulfoxide (DMSO) and 50 wt % sodium hydroxide aqueous solution 7.6 g (95 mmol) are added to product B obtained above, and the solution is agitated at 60° C. for 1 hour. 3-Bromo-2-methylpropene (95 mmol) is added, and the solution is agitated at 60° C. for 1 hour (h). A solution of sulfuric acid ($H_2SO_4$) 2.94 g (30 mmol)/$H_2O$ (20 ml) is then added to the solution and agitated at 60° C. for 2 h. Product C is deposited from the solution by acidolysis. The reaction mixture is filtered to obtain precipitated product C, which is used without further purification.

Synthesis of IC-3 and IC-4

To a solution of corresponding phenol (1 eq, for IC-3, the phenol is 2,6-di-tert-butylphenol and for IC-4 it is 2-tert-butyl-6-methylphenol) in DMF is added paraformaldehyde (1.5 eq), product C (1.5 eq) and HMTA (0.1 eq). The resulting solution is stirred at 120° C. for 8 hours. The reaction mixture is quenched by addition of water extracted with ethyl acetate. The combined organic layers are washed with brine, dried over $Na_2SO_4$, and concentrated under reduced pressure. The crude material is purified by flash column chromatography to obtain the desired product. 1H NMR for IC-3: (400 MHz, CDCl3) δ 7.31 (s, 2H), 5.26 (s, 1H), 5.00 (s, 2H), 4.88 (m, 2H), 4.75 (m, 2H), 4.44 (d, 4H), 1.76 (s, 6H), 1.42 (s, 18H). HRMS (m/z): calculated for $C_{26}H_{38}N_3O_4^+$[M+H+]: 456.2857; found 456.2849. 1H NMR for IC-4 (400 MHz, CDCl3): δ 7.29 (s, 1H), 7.10 (s, 1H), 5.00-4.85 (m, 5H), 4.74 (s, 2H), 4.44 (s, 4H), 2.21 (s, 3H), 1.76 (s, 6H), 1.38 (s, 9H).

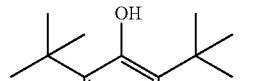

IC-1

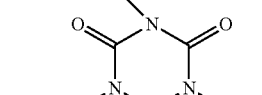

IC-2

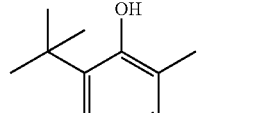

IC-3

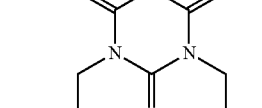

IC-4

Compounding and Pelletizing

For the samples with inventive compound IC-1, IC-2, IC-3 and IC-4, DXM-446 pellets and the compounds are pre-mixed in a single screw extruder at 120° C. and a screw speed of 15 revolutions per minute (rpm) for 10 minutes (min) and then mixed at 120° C. at a screw speed of 30 rpm for 4 min. The melt strand is extruded and fed into BRABENDER™ pelletizer to prepare the pellets. The pellets and DCP with a total weight of 50 g are then placed into a fluorinated high density polyethylene (HDPE) bottle and sealed. The materials are mixed homogeneously by hand shaking and soaked at 70° C. for 6 h.

For the comparative samples containing DXM-446, DCP, DAIC-EH and IRGANOX™ 1076, a similar soaking process is used. DCP, DAIC-EH and IRGANOX™ 1076 are mixed together and put in a 70° C. oven for several minutes to melt and form a homogeneous liquid, which is then mixed with DXM-446 pellets and soak at 70° C. for 6 h.

Moving Die Rheometer

Curing behavior is recorded by moving die rheometer (MDR) at 180° C. according to ASTM D5289 on an Alpha Technologies MDR2000 using soaked pellets. Similar tests are conducted at 140° C. to characterize a scorch time (the time required for the sample to achieve one unit increase in torque).

Scorch Improvement

Scorch improvement (SI) of sample X is calculated with Equation 1:

$$SI=(ts1@140° C.-ts1'@140° C.)/ts1'@140° C. \quad (Eq. 1)$$

wherein SI is scorch improvement, $ts1@140°$ C. is the determined scorch time by MDR at 140° C., $ts1'@140°$ C. is the predicted scorch time of a theoretical sample with the same formulations as sample X but no scorch retardant compounds, where the prediction is based on the crosslinking (MH-ML) density of sample X. $ts1'@140°$ C. is given by Equation 2:

$$ts1'@140° C.=0.0173137+65.038742/(MH-ML@180° C.) \quad (Eq. 2)$$

where (MH-ML@180° C.) is the crosslinking density of sample X measured via MDR at 180° C. Equation 2 is determined based on the relationship between scorch time TS1 and crosslinking density (MH-ML) of six samples prepared with only DXM-446 and DCP. The sample formulations are listed in Table 1 and analyzed with the JMP™ statistical discovery software. The relationship between ts1 and (MH-ML) is reciprocal and Equation 2 is obtained by the "Fit special—Reciprocal" function in JMP™. The curve indicating the relationship between ts1 and (MH-ML) was presented in the FIG. 1. The fitting method is described in WO 2014/040532. By this method Equation 2 is obtained which is used to calculate ts1'.

TABLE 1

Scorch Improvement Equation 2 Determination Samples

|  | SIS-1 | SIS-2 | SIS-3 | SIS-4 | SIS-5 | SIS-6 |
|---|---|---|---|---|---|---|
| DXM-446 | 99.35 | 99.00 | 98.50 | 98.30 | 98.00 | 97.50 |
| DCP | 0.65 | 1.00 | 1.50 | 1.70 | 2.00 | 2.50 |
| Total | 100.00 | 100.00 | 100.00 | 100.00 | 100.00 | 100.00 |
| ML, dN*m | 0.24 | 0.25 | 0.25 | 0.26 | 0.26 | 0.26 |
| MH, dN*m | 1.84 | 2.82 | 3.85 | 4.32 | 5.03 | 5.51 |
| MH − ML, dN*m | 1.60 | 2.57 | 3.60 | 4.06 | 4.77 | 5.25 |
| ts1/180° C., min | 2.14 | 1.27 | 0.94 | 0.93 | 0.81 | 0.78 |
| T90/180° C., min | 4.06 | 4.26 | 4.02 | 4.14 | 3.99 | 3.95 |
| ts1/140° C., min | 41.09 | 24.49 | 17.95 | 15.69 | 14.23 | 12.71 |

Regards to the SI value calculated from Equation 1, a negative SI indicates worse anti-scorch property while a positive SI indicates an improvement in anti-scorch property, with higher positive SI values preferred for superior end use performance.

Comparative Examples and Inventive Examples

TABLE 2

Comparative formulations 1-5 and inventive formulations 1-8

|  | CF1 | CF2 | CF3 | CF4 | CF5 | IF1 | IF2 | IF3 | IF4 | IF5 | IF6 | IF7 | IF8 |
|---|---|---|---|---|---|---|---|---|---|---|---|---|---|
| DXM-446 | 98.80 | 98.52 | 97.96 | 98.52 | 97.96 | 98.58 | 98.14 | 98.60 | 98.20 | 98.57 | 98.11 | 98.59 | 98.17 |
| DCP | 1.20 | 1.20 | 1.20 | 1.20 | 1.20 | 1.20 | 1.20 | 1.20 | 1.20 | 1.20 | 1.20 | 1.20 | 1.20 |
| IRGANOX ™ 1076 |  | 0.28 | 0.84 |  |  |  |  |  |  |  |  |  |  |
| DAIC-EH |  |  |  | 0.17 | 0.50 |  |  |  |  |  |  |  |  |
| IC-1 |  |  |  |  |  | 0.22 | 0.66 |  |  |  |  |  |  |
| IC-2 |  |  |  |  |  |  |  | 0.20 | 0.60 |  |  |  |  |
| IC-3 |  |  |  |  |  |  |  |  |  | 0.23 | 0.69 |  |  |
| IC-4 |  |  |  |  |  |  |  |  |  |  |  | 0.21 | 0.63 |
| Total | 100.00 | 100.00 | 100.00 | 100.00 | 100.00 | 100.00 | 100.00 | 100.00 | 100.00 | 100.00 | 100.00 | 100.00 | 100.00 |
| ML, dN*m | 0.26 | 0.22 | 0.21 | 0.23 | 0.22 | 0.22 | 0.21 | 0.21 | 0.19 | 0.22 | 0.21 | 0.21 | 0.20 |
| MH, dN*m | 3.32 | 3.09 | 2.68 | 2.79 | 1.95 | 3.53 | 3.94 | 3.32 | 2.83 | 3.71 | 3.97 | 3.06 | 2.71 |
| MH − ML, dN*m | 3.06 | 2.87 | 2.47 | 2.56 | 1.73 | 3.31 | 3.73 | 3.11 | 2.64 | 3.49 | 3.76 | 2.85 | 2.51 |
| ts1/180° C., min | 1.15 | 1.19 | 1.36 | 1.36 | 2.10 | 1.06 | 1.08 | 1.25 | 1.74 | 1.10 | 1.16 | 1.45 | 1.85 |
| t90/180° C., min | 4.30 | 4.8 | 4.39 | 4.49 | 4.70 | 4.19 | 4.15 | 4.25 | 4.89 | 4.11 | 4.11 | 3.32 | 4.83 |
| ts1/140° C., min | 19.40 | 37.95 | 59.6 | 40.76 | 80.14 | 31.03 | 47.92 | 46.16 | 88.35 | 35.54 | 50.42 | 56.21 | 113.16 |
| SI | −0.09 | 0.67 | 1.26 | 0.60 | 1.13 | 0.58 | 1.75 | 1.21 | 2.58 | 0.91 | 1.91 | 1.46 | 3.36 |

Comparative sample CF1 is a formulation with only DXM-446 and DCP. The MH-ML at 180° C. is 3.06 and ts1 at 140° C. is 19.40 min. The SI value, calculated according to Equation 1, is −0.09 which means that the ts1 is close to the ts1' curve.

Comparative samples CF2 and CF3 are formulations with DXM-446, DCP, IRGANOX™ 1076 (hindered phenol antioxidant) and DAIC-EH (curing coagent). IRGANOX™ 1076 also plays a role of scorch retardant. The curing/scorch balance achieved by phenol and coagents are shown in CF2 and CF3 in Table 2. The SI is about 0.67 and 1.26, respectively, and as compared with the SI of CF1, significant improvement in scorch resistance is shown.

Comparative sample CF4 and CF5 are formulations with DXM-446, DCP and IRGANOX™ 1076. IRGANOX™ 1076 plays a role as scorch retardant. SI is 0.6 and 1.13 at lower and higher loading, respectively, suggesting the scorch improvement compared to CF1.

However once these two functions are combined together into one molecule (IC-1), a new curing/scorch balance is achieved. For IF1 and IF2, both curing (MH) and scorch time (ts1@140° C.) increased compared with CF1. This is totally different from CF2 and CF3, introducing these two functions separately, scorch time increases at a cost of crosslinking density (MH) decrease. Moreover, as is seen from ts1/180° C. and T90/180° C. the cure time is obviously shortened by the addition of IC-1 (comparing IF1 and CF2, IF2 and CF3, respectively). These results suggest a desired performance and a synergy between phenol and DAIC once they are combined into one molecule.

Similar improvements can be seen by the use of IC-2 with a semi hindered phenol. Although curing (MH) decreased when introducing IC-2, the significant increase in scorch time also suggests a new balance between curing time (MH) and scorch time (ts1/140° C.). Compared with CF1, the SI significantly increased from –0.09 to 1.21 in IF3 further to 2.58 in IF4.

SI of IF5 and IF6 increases to 0.91 and 1.91, respectively, with the incorporation of IC-3. The formulations also demonstrate that both the curing and scorch time are improved. Furthermore, T90@180° C. is obviously shortened compared to the control formulations, which suggest potentially fast curing properties.

SI of IF7 and IF8 increases to 1.46 and 3.36, respectively, which demonstrate very significant scorch improvement. Also for IF7, potentially fast curing can be achieved according to t90@180° C.

TABLE 3

Comparative Formulation 6 and Inventive Formulation 9

|  | CF6 | IF9 |
|---|---|---|
| DXM-446 | 97.94 | 97.85 |
| DCP | 1.7 | 1.7 |
| Cyanox ™ 1790 | 0.14 |  |
| IC-2 |  | 0.23 |
| DSTDP | 0.22 | 0.22 |
| Total | 100.00 | 100.00 |
| ML, dN*m | 0.21 | 0.21 |
| MH, dN*m | 3.39 | 4.08 |
| MH – ML, dN*m | 3.18 | 3.87 |
| ts1/180° C., min | 1.25 | 1.06 |
| T90/180° C. | 4.31 | 4.05 |
| ts0.5/140° C. | 20.12 | 22.99 |
| ts1/140° C. | 34.86 | 35.34 |

Table 3 reports Comparative Formulation 6 with CYANOX™ 1790 and Inventive Formulation 9 with IC-2. Both formulations contain distearyl thiodipropionate (DSTDP) as the antioxidant. Compared to CF6, IF9 improved significantly in curing (MH-ML) and reports an obvious improvement in T90/180° C.

In general, phenol and DAIC in one molecule change the balance of cure and scorch time as compared to their introduction to the ethylene-based polymer as two separate molecules. By introducing a single additive containing both phenol and DAIC, simultaneous improvements of scorch resistance and curing density are achieved.

The invention claimed is:

1. A composition comprising:
    (A) An ethylene-based polymer,
    (B) A peroxide, and
    (C) a hybrid scorch retardant/cure coagent selected from at least one compound of Formula IC-2, IC-3, or IC-4:

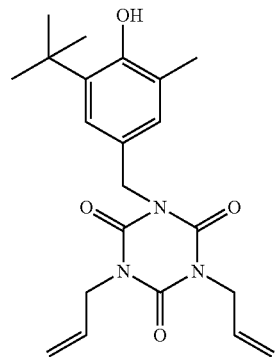

(Formula IC-2)

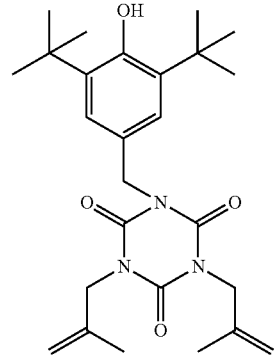

(Formula IC-3)

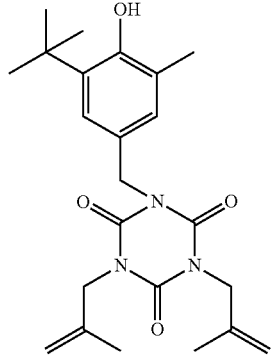

(Formula IC-4)

wherein the composition comprises from 0.20 to 0.25 weight percent of the hybrid scorch retardant/cure coagent, the composition, when crosslinked, having a crosslinking density expressed as "MH-ML@180° C." from 2.85 dN·m to 3.49 dN·m.

2. An article compromising the composition of claim 1.

3. The article of claim 2 in the form of a wire or cable sheath.

4. A composition comprising:

(A) An ethylene-based polymer, (B) A peroxide, and (C) a hybrid scorch retardant/cure coagent selected from at least one compound of Formula IC-2, IC-3, or IC-4:

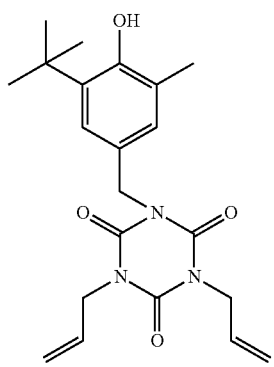

(Formula IC-2)

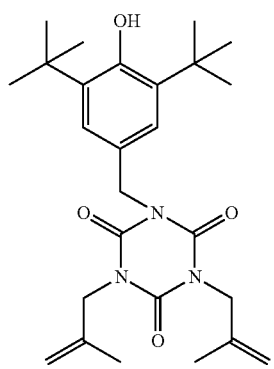

(Formula IC-3)

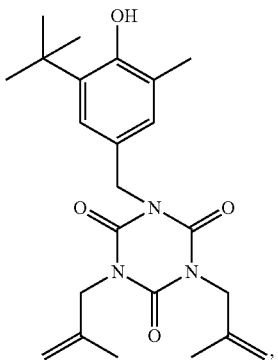

(Formula IC-4)

wherein the composition comprises from 0.60 to 0.70 weight percent of the hybrid scorch retardant/cure coagent, the composition, when crosslinked, having a crosslinking density expressed as "MH-ML@180° C." from 2.51 dN·m to 3.76 dN·m.

* * * * *